United States Patent [19]

Rothenberg et al.

[11] 4,267,372

[45] May 12, 1981

[54] PREPARATION OF N-SUBSTITUTED ACRYLAMIDE MONOMERS HAVING CATIONIC SUBSTITUENTS

[75] Inventors: Alan S. Rothenberg, Wilton; Michael N. Desmond, Norwalk, both of Conn.

[73] Assignee: American Cyanamid Company, Stamford, Conn.

[21] Appl. No.: 88,738

[22] Filed: Oct. 26, 1979

[51] Int. Cl.$^3$ ............... C07C 102/00; C07C 102/04; C07C 102/06
[52] U.S. Cl. ............... 564/205; 260/326.2; 544/168; 546/247
[58] Field of Search ............... 260/561 N, 326.2; 546/247; 544/168; 564/205

[56] References Cited

U.S. PATENT DOCUMENTS

| | | | |
|---|---|---|---|
| 3,878,247 | 4/1975 | Moss et al. | 260/561 N |
| 4,031,138 | 6/1977 | Nieh et al. | 260/561 N |
| 4,180,643 | 12/1979 | Moss et al. | 260/561 N |

*Primary Examiner*—Arthur P. Demers
*Attorney, Agent, or Firm*—Paul W. Leuzzi, II

[57] ABSTRACT

Reaction of a beta-aminopropionamide with an acrylic acid or its derivative provides an N-substituted acrylamide monomer having cationic substituents attached thereto. The instant reaction occurs under mild processing conditions at a temperature between about 160° C. and 230° C.

10 Claims, No Drawings

PREPARATION OF N-SUBSTITUTED ACRYLAMIDE MONOMERS HAVING CATIONIC SUBSTITUENTS

BACKGROUND OF THE INVENTION

This invention generally relates to an improved process for making certain cationic monomers. More particularly, this invention relates to an improved process for preparing N-substituted acrylamide monomers having cationic substituents attached thereto.

Cationic monomers are desired for preparing water-soluble cationic polymers useful in a number of applications, particularly in water treatment. Many cationic monomers are available and a variety of cationic polymers result directly therefrom or by suitable modification of these polymers. In certain applications including water treatment, cationic polymers must be resistant to hydrolysis in order to provide the properties for which their cationic character is chosen. A particularly desirable class of cationic monomers for making such polymers are those described as N-substituted acrylamides having cationic substituents. These monomers and their preparation are currently well known in the art.

In U.S. Pat. No. 3,878,247 issued Apr. 15, 1975 to P. H. Moss and R. M. Gipson, there is described a non-catalytic process for the preparation of N(tertiaryaminoalkyl) acrylamides which comprises subjecting a corresponding betaaminopropionamide to a temperature of about 180°–300° C. and separating the N-(tertiaryaminoalkyl) acrylamide from the reaction product. It also discloses that the corresponding aminopropionamide compounds can be made by reacting at least two moles of a tertiaryaminoalkyl amine with an acrylic acid or ester compound. The process is said to provide the desired compounds in high yields with minimal back-addition or polymerization.

The reference process thermally cracks a betaaminopropionamide to provide one mole of the desired monomer and one mole of tertiaryaminoalkyl amine for each mole of beta-aminopropionamide cracked. Such processing requires extremely harsh reaction conditions to be employed and theoretically restricts the amount of desired product that can be produced in a reaction vessel during a batch reaction to one mole of cationic monomer per mole of beta-aminopropionamide charged, although in actuality somewhat less than this amount is recovered.

An alternative method for producing cationic monomers, such as cationic methacrylamide, known in the art is the thermal decomposition of N-(dialkylaminoalkyl)-2-methylbeta-alanine. As described in U.S. Pat. No. 3,652,671, issued to Barron in 1972, this process proceeds through a rearrangement mechanism by heating the starting materials to between 140°–230° C.

Accordingly, there exists the need for a process which can provide a greater quantity of the desired cationic monomer per reaction given equimolar amounts of beta-aminopropionamide under milder reaction conditions and without the need for the recycling of reaction products. Such a provision would fulfill a long-felt need and constitute a significant advance in the art.

SUMMARY OF THE INVENTION

The instant invention provides a process for preparing a cationic monomer of the general structure:

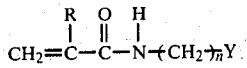

wherein R is hydrogen or methyl, n is an integer of from 2 to 6 inclusive, and Y is selected from the group consisting of morpholine, pyrrolidine, piperidine and

wherein R' and R" are individually saturated aliphatic radicals containing from 1 to 4 carbon atoms inclusive, which process comprises reacting a compound of the general structure:

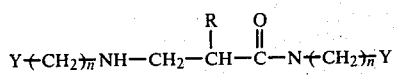

wherein R, n and Y are of the same significance as previously set forth, with an equal molar amount of a compound of the general structure:

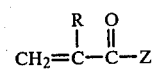

wherein R is of the same significance as previously set forth and Z is selected from the group consisting of —OH, —OR''' and —X wherein R''' is a saturated aliphatic radical having one or two carbon atoms and X is a halogen under suitable reaction conditions and either distilling off the corresponding water or alcohol or neutralizing the hydrogen halide formed.

DETAILED DESCRIPTION OF THE INVENTION

In accordance with the present invention, there is provided a process for preparing the cationic monomer of structure I by reacting equal molar amounts of compounds of structures II and III, respectively.

The process of the present invention can provide two moles of desired cationic monomer for each mole of beta-aminopropionamide starting material employed thus doubling the potential quantity of desired product from the amount of starting material employed. In addition, since the N-(tertiaryaminoalkyl) amine preferentially engages in a condensation reaction with the —Z function of the added CH$_2$=CR—COZ, the possibility of back-reaction of the N-(tertiaryamino-alkyl) amine with the monomer produced is minimized. Addition of the CH$_2$=CR—COZ compound to the starting beta-aminopropionamide enables the desired product to be obtained at lower temperatures and in shorter times than when the aminopropionamide is cracked alone.

In carrying out the process of the present invention, the starting material, beta-aminopropionamide, is prepared according to conventional procedures. A conventional procedure which is highly effective is to react at least two moles, and preferably an excess, of a N-(tertiaryaminoalkyl) amine with one mole of an acrylic acid or an acrylic ester. This reaction is preferably carried out at reflux with the continuous removal of water or alcohol generated by reaction. In the procedure, two reactions occur: one reaction involves the Michael addition of one mole of the N-(tertiaryaminoalkyl) amine to the double bond of the acrylic acid or ester and another reaction involves condensation of one mole of the N-(tertiaryaminoalkyl) amine with the acid or ester group of the acrylic acid or ester. When an acrylic acid is employed, water will be the product of condensation removed during reflux, while an alcohol will be the product so removed when the acrylic ester is employed. Under appropriate conditions for the reactants employed, the desired beta-aminopropionamide can be obtained in substantially quantitative yield within a suitable time period. After the reaction is complete and no further removal of water or alcohol is apparent, a rapid temperature rise will begin. At this time, it is desirable to reduce the pressure on the reaction medium so as to strip off excess N-(tertiaryaminoalkyl) amine that may be present. After stripping off excess amine is complete, the product recovered will be essentially pure beta-aminopropionamide. However, it is not necessary to recover the reaction product, since the process to provide the desired cation ionic monomer can be run on the pot mixture as obtained.

The reactions of N-(tertiaryaminoalkyl) amine and acrylic acid or ester can be illustrated by the following general equations, it being understood that the two reactions may occur simultaneously or in any order.

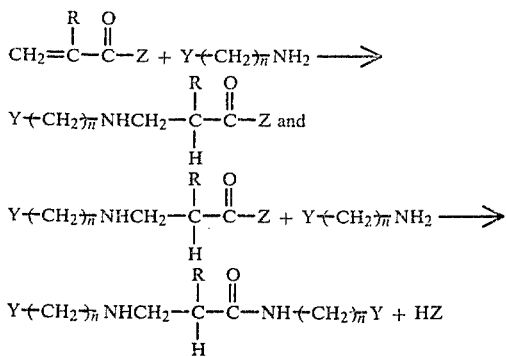

wherein R, Y, Z and n are of the same significance as set forth above.

After the desired beta-aminopropionamide is obtained according to conventional procedures, processing according to the desired monomer is recovered in a known manner. It is to be understood that the beta-aminopropionamide need not be prepared immediately preceding processing by the present invention, but it may be obtained from any available source or prepared as needed.

To carry out the preparation of the cationic monomer according to the process of the present invention, a predetermined amount of the beta-aminopropionamide is placed in a suitable reactor. To the reactor is then charged a molar equivalent of an acrylic acid, acrylic acid ester, or acrylic acid halide. The reaction mixture is then heated to a temperature in the range of from about 160° C. to about 210° C. while continuously removing the by-product resulting from the condensation reaction by either distillation or neutralization. In conducting this process, the reaction may occur by one of two possible pathways with either or both contributing to the formation of the product while not wishing to be bound by any particular theory or reaction. In the first possible pathway, the beta-aminopropionamide may be decomposed to form one mole of cationic monomer and one mole of N-(tertiaryaminoalkyl) amine which latter compound simultaneously or subsequently condenses with the acrylic compound to form a second mole of cationic monomer. The second pathway provides for the acylation of the beta-aminopropionamide by the acrylic compound to form an intermediate which thereafter decomposes to form two moles of cationic monomer as set forth below.

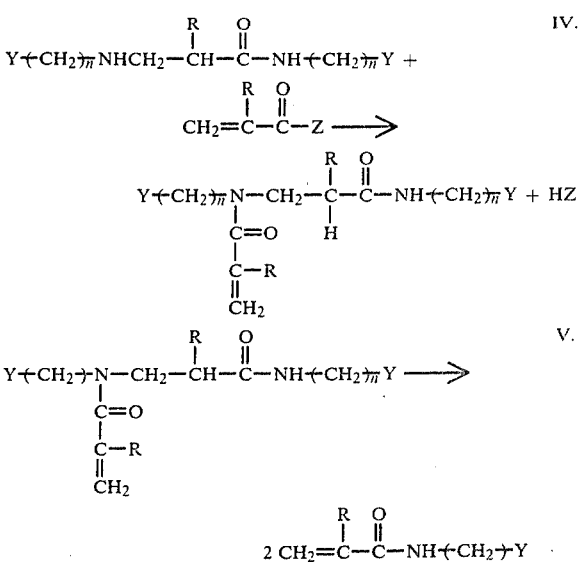

wherein R, Y, Z and n have the same significance as set forth previously.

After co-condensation (IV) and cracking (V) reactions are completed, as described above, the reaction product may be further purified, if desired, by fractional distillation or such other purification procedures as are appropriate.

The product obtained by the process of the present invention is a cationic N-substituted acrylamide with substituents that provide a cationic nature thereto. Such product is readily polymerizable to high molecular weight water-soluble polymers which are useful in numerous applications. The polymers are resistant to degradation by hydrolysis over a wide pH range and are, therefore, useful in applications wherein hydrolyzable polymers are ineffective.

The process of the present invention, in addition to providing increased amounts of desired cationic monomer per mole of beta-aminopropionamide employed, also enables the production of cationic monomer to proceed at lower temperature and/or in shorter time periods.

The following specific examples illustrate certain aspects of the present invention and, more particularly, point out methods of evaluating the unique advantages of preparing the cationic monomer according to the present invention. However, the examples are set forth for illustration only, and are not to be construed as limitations on the present invention except as set forth in the appended claims. All parts and percentages are by weight unless otherwise specified.

EXAMPLE A

Preparation of beta-(dimethylaminopropylamino)-N-(dimethyl-aminopropyl)-alpha-methylpropionamide.

1000 Parts of methyl methacrylate and 2550 parts of dimethylaminopropylamine are refluxed with 2.72 parts of N,N'-diphenyl-p-phenylenediamine for one hour under total reflux. The head is then set for takeoff below 65° C. and 297 parts of liberated methanol are collected over an 8 hour period until the pot temperature begins to rise rapidly, at which time the pressure is gradually reduced to 10 mm Hg over a 2 hour period to strip off 569 parts of excess dimethyl-aminopropylamine. Analysis of the remaining pot mixture shows it to consist of 2609 parts of 96% pure beta-aminopropionamide.

EXAMPLE 1

Preparation of N-(dimethylaminopropyl) methacrylamide.

700 Parts of the beta-aminopropionamide collected in Example A are placed in a flask fitted with a nitrogen inlet, addition funnel, vigreux column, and mechanical stirrer. To this, 221 parts of methacrylic acid are then added over a 10 minute period with ice bath cooling. The temperature is then raised to 200°-215° C. and 45 parts of water are continuously distilled from the mixture over a 1½ hour period. Fractional distillation of the pot mixture yielded 597 parts of N-(dimethylaminopropyl)-methacrylamide.

COMPARATIVE EXAMPLE A

A reaction flask identical to that employed in Example 1 is filled with 700 parts of the beta-aminopropionamide intermediate collected in Example A, and 221 parts of methacrylic acid. The flask is evacuated to 25 mm. and gradually heated to a pot temperature of 250° C. over a five (5) hour period. During this period the cracked product is distilled overhead. Distillation of the crude cracked product yielded 403 parts of N-(dimethylaminopropyl) methacrylamide. This yield represents 67.5% of the quantity of monomer obtained from the same amount of starting materials in Example 1.

EXAMPLE 2

In each of 2 test tubes is placed 0.68 parts of the distilled beta-aminopropionamide prepared from methyl methacrylate and dimethylaminopropylamine of Example A. 0.215 Parts of methacrylic acid is added to one of the test tubes and then both are sealed with septa and flushed with nitrogen for 15 minutes through syringe needles. The tubes are simultaneously immersed in an oil bath maintained at 170° C. and samples taken from each by syringe after 3 and 10 hours of heating, respectively. Analysis of the samples showed that those samples taken from the test tube lacking methacrylic acid had not undergone any reaction and were still pure beta-aminopropionamide, while the 3 hour sample from the test tube initially containing methacrylic acid contained 26 mole percent N-(dimethylaminopropyl) methacrylamide and the 10 hour sample contained 40 mole percent of the same cationic monomer.

EXAMPLE 3

The procedure of Example 1 is again followed except that there is now employed in place of the methacrylic acid an equimolar amount of methyl methacrylate. Although methanol is distilled from the mixture instead of water the results are substantially equivalent.

EXAMPLE 4

The procedure of Example 1 is again followed except that there is now employed in place of the methacrylic acid an equimolar amount of methacryloyl chloride. A sufficient amount of 10% aqueous sodium carbonate solution is added to the reaction medium to neutralize the hydrogen chloride liberated during the reaction. Results are substantially equivalent to those of Example 1.

EXAMPLES 5-9

Following the procedure of Example 1, a series of beta-aminopropionamides are prepared and converted to the appropriate cationic monomer. The reactions employed and the products obtained are given in Table I which follows. In each instance, yields of aminopropionamide and cationic monomer are in excess of 75% and 50%, respectively.

TABLE I

| | β-PROPIONAMIDE PREPARATION | | CATIONIC MONOMER PREPARATION | |
|---|---|---|---|---|
| EXAMPLE | ACRYLIC COMPOUND | AMINE | ACRYLIC COMPOUND | PRODUCT |
| 5 | $CH_2=CH-COOH$ | $(CH_3)_2N(CH_2)_2NH_2$ | $CH_2=CH-COOH$ | $CH_2=CH-CONH(CH_2)_2N(CH_3)_2$ |
| 6 | $CH_2=CHCOOCH_3$ | $(CH_3CH_2)_2N(CH_2)_3NH_2$ | $CH_2=CH-COOH$ | $CH_2=CH-CONH(CH_2)_3N(CH_2CH_3)_2$ |
| 7 | $CH_2=\underset{\underset{CH_3}{\mid}}{C}-COOCH_3$ | $(CH_3)_2N(CH_2)_6NH_2$ | $CH_2=\underset{\underset{CH_3}{\mid}}{C}-COOH$ | $CH_2=\underset{\underset{CH_3}{\mid}}{C}-CONH(CH_2)_6N(CH_3)_2$ |
| 8 | $CH_2=\underset{\underset{CH_3}{\mid}}{C}-COOCH_3$ | $O\diagup\hspace{-2pt}\diagdown N(CH_2)_3NH_2$ | $CH_2=\underset{\underset{CH_3}{\mid}}{C}-COOH$ | $CH_2=\underset{\underset{CH_3}{\mid}}{C}-CONH(CH_2)_3N\diagup\hspace{-2pt}\diagdown O$ |
| 9 | $CH_2=\underset{\underset{CH_3}{\mid}}{C}-COOCH_3$ | ⬡N(CH_2)_2NH_2 | $CH_2=\underset{\underset{CH_3}{\mid}}{C}-COOH$ | $CH_2=\underset{\underset{CH_3}{\mid}}{C}-CONH(CH_2)_2N$⬡ |

We claim:

1. A process for preparing a cationic monomer of the general structure:

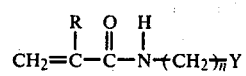

wherein R is hydrogen or methyl, n is an integer of from 2 to 6, inclusive, Y is selected from the group consisting of morpholine, pyrrolidone, piperidine and

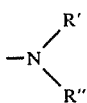

wherein R' and R" are individually saturated aliphatic radicals containing from 1 to 4 carbon atoms inclusive, which process comprises reacting a compound of the general structure:

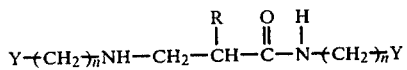

wherein R, Y and n are of the same significances previously set forth with an equal molar amount of a compound of the general structure:

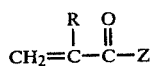

wherein R is the same as above and Z is selected from the group consisting of —OH, —OR''' and —X wherein R''' is a saturated aliphatic radical having one or two carbon atoms, and —X is a halogen under reaction temperatures within the range of about 160°–230° C. and either distilling off the corresponding water or alcohol or neutralizing the hydrogen halide formed.

2. The process of claim 1 wherein said R is methyl, said n is 3, said Y is

and said R' and R" are both methyl groups.

3. The process of claim 1 wherein said Z is —OH.
4. The process of claim 1 wherein said Z is —OR'''.
5. The process of claim 4 wherein said R''' is methyl.
6. The process of claim 1 wherein said Z is —X.
7. The process of claim 6 wherein said X is chlorine.
8. The process of claim 1 wherein said R is methyl, said n is 3, said Y is

said R' and R" are methyl groups and said Z is —OH.

9. The process of claim 1 wherein said R is hydrogen, said n is 2, said Y is

said R' and R" are methyl groups and said Z is OH.

10. The process of claim 1 wherein said R is hydrogen, said n is 3, said Y is

said R' and R" are ethyl groups, and said Z is —OH.

* * * * *

UNITED STATES PATENT OFFICE
CERTIFICATE OF CORRECTION

Patent No. 4,267,372                      Dated May 12, 1981

Inventor(s) ALAN SOL ROTHENBERG & MICHAEL NIALL DESMOND O'CONNOR

It is certified that error appears in the above-identified patent and that said Letters Patent are hereby corrected as shown below:

On the title page, after "Inventors:", please delete "Michael N. Desmond" and insert therefor -- Michael N. D. O'Connor --.

Signed and Sealed this

Twenty-fifth Day of August 1981

[SEAL]

Attest:

GERALD J. MOSSINGHOFF

Attesting Officer      Commissioner of Patents and Trademarks

UNITED STATES PATENT OFFICE
CERTIFICATE OF CORRECTION

Patent No. 4,267,372　　　　　　　　Dated May 12, 1981

Inventor(s) ALAN SOL ROTHENBERG & MICHAEL NIALL DESMOND O'CONNOR

It is certified that error appears in the above-identified patent and that said Letters Patent are hereby corrected as shown below:

Column 5, line 35, please delete "700" and insert therefor -- 921 --.

Column 5, line 36-37, please delete ",221 parts of methacrylic acid".

Column 6, line 68, please delete "pyrrodidone" and insert therefor -- pyrrolidine --.

Signed and Sealed this

Seventeenth Day of November 1981

[SEAL]

Attest:

Attesting Officer

GERALD J. MOSSINGHOFF

Commissioner of Patents and Trademarks